United States Patent
Enomoto (10) Patent No.: US 9,567,277 B2
(45) Date of Patent: *Feb. 14, 2017

(54) REAGENT FOR ENHANCING GENERATION OF CHEMICAL SPECIES

(71) Applicant: TOYO GOSEI CO., LTD., Ichikawa-shi (JP)

(72) Inventor: Satoshi Enomoto, Chiba (JP)

(73) Assignee: TOYO GOSEI CO., LTD., Ichikawa-shi, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/508,445

(22) Filed: Oct. 7, 2014

(65) Prior Publication Data

US 2015/0099893 A1   Apr. 9, 2015

Related U.S. Application Data

(60) Provisional application No. 61/961,220, filed on Oct. 8, 2013.

(51) Int. Cl.

| | | |
|---|---|---|
| *C07C 43/205* | (2006.01) | |
| *C07D 335/12* | (2006.01) | |
| *C07C 69/54* | (2006.01) | |
| *G03F 7/004* | (2006.01) | |
| *G03F 7/039* | (2006.01) | |
| *G03F 7/095* | (2006.01) | |
| *G03F 7/20* | (2006.01) | |

(52) U.S. Cl.
CPC ........... *C07C 43/2055* (2013.01); *C07C 69/54* (2013.01); *C07D 335/12* (2013.01); *G03F 7/0045* (2013.01); *G03F 7/0397* (2013.01); *G03F 7/095* (2013.01); *G03F 7/203* (2013.01)

(58) Field of Classification Search
CPC .................................................. C07C 43/2055
USPC ....................................................... 549/16, 26
See application file for complete search history.

(56) References Cited

U.S. PATENT DOCUMENTS

| | | |
|---|---|---|
| 5,914,807 A | 6/1999 | Downing |
| 7,851,252 B2 | 12/2010 | Nealey et al. |
| 2015/0060728 A1 | 3/2015 | Enomoto et al. |
| 2015/0099893 A1 | 4/2015 | Enomoto |
| 2015/0140493 A1 | 5/2015 | Enomoto et al. |
| 2015/0241779 A1 | 8/2015 | Enomoto |
| 2016/0070165 A1 | 3/2016 | Enomoto |
| 2016/0147144 A1 | 5/2016 | Enomoto |
| 2016/0159953 A1 | 6/2016 | Enomoto et al. |
| 2016/0187773 A1 | 6/2016 | Enomoto |
| 2016/0194300 A1 | 7/2016 | Enomoto |
| 2016/0195808 A1 | 7/2016 | Enomoto |
| 2016/0223904 A1 | 8/2016 | Enomoto |
| 2016/0225611 A1 | 8/2016 | Enomoto et al. |

FOREIGN PATENT DOCUMENTS

| | | |
|---|---|---|
| WO | 2014185065 A1 | 11/2014 |
| WO | 2014208076 A1 | 12/2014 |
| WO | 2014208102 A1 | 12/2014 |
| WO | 2014208103 A1 | 12/2014 |
| WO | 2015019616 A1 | 2/2015 |
| WO | 2015022779 A1 | 2/2015 |
| WO | 2015052914 | 4/2015 |

OTHER PUBLICATIONS

Shin et al., Bull. KR Chem. Soc. (1981), vol. 2(3), pp. 114-121.*
Kharchenko et al., KhimiyaGeterotsiklicheskihk Soedinenii (1970), vol. 3, pp. 338-341.*
U.S. Appl. No. 14/311,051, Reagent for Enhancing Generation of Chemical Species, 17 pages, filed Jun. 20, 2014.
U.S. Appl. No. 14/476,607, Reagent for Enhancing Generaton of Chemical Species, 16 pages, filed Sep. 3, 2014.
Shin et al., Bull, KR Chem. Soc. (1981), vol. 2(3), pp. 114-121.
Kharchenko et al., Khimiya Geterotsiklicheskikh Soedinenii (1970), vol. 3, pp. 338-341.
Office Action for U.S. Appl. No. 14/547,088 dated Jan. 20, 2016.
Office Action for U.S. Appl. No. 14/476,607 dated Jan. 29, 2016.
Photoacid Generator Selection Guide for the electronics industry and energy curable coatings, BASF catalog, 2010, Wyandotte, MI, US.
U.S. Appl. No. 15/027,855, Reagent for Enhancing Generation of Chemical Species and Manufacturing Apparatus, filed Apr. 7, 2016, available on the U.S. Patent Office website.

\* cited by examiner

*Primary Examiner* — Taofiq A Solola
(74) *Attorney, Agent, or Firm* — Traskbritt P.C.

(57) ABSTRACT

A reagent that enhances acid generation of a photoacid generator and composition containing such a reagent is described.

10 Claims, 3 Drawing Sheets

REAGENT FOR ENHANCING GENERATION OF CHEMICAL SPECIES

CROSS-REFERENCE TO RELATING APPLICATION

This patent application claims the benefit under 35 U.S.C. §119(e) of U.S. Provisional Patent Application Ser. No. 61/961,220 filed on Oct. 8, 2013, the disclosure of which is hereby incorporated herein in its entirety by this reference.

TECHNICAL FIELD

An aspect hereof relate to the fields of chemistry and a reagent that can produce an intermediate that enhances generation of a chemical species, such as an acid and base, from a precursor. Such intermediate can transfer its energy or electron to the precursor or accept the precursor's energy or electron. Such transfer or acceptance of energy or electron involved with the precursor and the intermediate generates the chemical species. The application further relates to a reagent that enhances acid generation of a photoacid generator and composition containing such a reagent.

BACKGROUND

Current high-resolution lithographic processes are based on chemically amplified resists ("CARs") and are used to pattern features with dimensions less than 100 nm.

Methods for forming pattern features with dimensions less than 100 nm is disclosed in U.S. Pat. No. 7,851,252 to Nealey et al. (Dec. 14, 2010), the entirety of the contents of which are incorporated herein by this reference.

BRIEF SUMMARY

A reagent relating an aspect hereof is characterized as follows: the reagent is capable of generating a first chemical species; and a first cutoff wavelength in a first absorption spectrum of the reagent is shorter than a second cutoff wavelength of a second absorption spectrum of the first chemical species.

An example of an advantage of using the first chemical species having the second cutoff wavelength longer than the first cutoff wavelength is to enable it to enhance electron-transfer or energy-transfer involved with the first chemical species because of higher level of the highest occupied molecular orbital (HOMO) or lower level of the lowest unoccupied molecular orbital.

With regard to such a reagent, it is preferred that the first chemical species is selected from the group consisting of radical, ion, and a reactive intermediate containing an atom with unusual valence. An example of an advantage of using such a reactive intermediate is to enable it to enhance electron-transfer or energy-transfer involved with the first chemical species because of stronger interaction of the first chemical species with another molecule.

With regard to such a reagent, it is preferred that the first chemical species is capable of generating a first product. An example of an advantage of formation of such a first product is to enable it to use such a first product as a catalyst or sensitizer to induce or enhance a desired reaction. In such example, such a first product can function as a photosensitizer.

With regard to such a reagent, it is preferred that the first cutoff wavelength is shorter than a third cutoff wavelength in an absorption spectrum of the first product. An example of an advantage of using the first product having longer cutoff wavelength is enable to excite the first product because the first product can be excited by a light commonly used.

With regard to such a reagent, it is preferred that a first conjugation length of the reagent be shorter than a second conjugation length of the first product. In other words, the first product has an extended conjugated system. This may enable the reagent to easily generate the first product.

With regard to such a reagent, it is preferred that the reagent has a first pi-electron system; and the first product has the first pi-electron system and a second pi-electron system. An example of an advantage of using the first product having the second pi-electron system in addition to the first pi-electron system is to enable it to excite the first product by a light of which wavelength is longer.

With regard to such a reagent, it is preferred that the first pi-electron system is conjugated with the second pi-electron system in the first product. In other words, the first product has an extended conjugated system. An example of an advantage of using such a first product in which the second pi-electron system is conjugated with the first pi-electron system is to enable it to lower excitation energy of the first product.

With regard to such a reagent, it is preferred that the second pi-electron system is constituted by a carbon-carbon multiple bond. A typical example of such a carbon-carbon-multiple bond is a carbon-carbon double bond.

With regard to such a reagent, it is preferred that a first level of the highest occupied molecular orbital (HOMO) of the reagent is lower than a second level of the highest occupied molecular orbital (HOMO) of the first product. An example of an advantage of using such a first product having HOMO of which level is higher is to enable it to ease an electron-transfer from the first product.

With regard to such a reagent, it is preferred that the lowest excitation energy to excite the reagent is greater than the lowest excitation energy to excite the first product. An example of an advantage of the reagent which can be excited by higher excitation energy is to enable it to make a film formed of a composition containing such a reagent highly transparent.

With regard to such a reagent, it is preferred that the first product further has a third pi-electron system. An example of an advantage of using the first product that further includes the third pi-electron system is to enable it to lower excitation energy of the third product.

With regard to such a reagent, it is preferred that the third pi-electron system is conjugated with the second pi-electron system. An example of an advantage of using the first product in which the third pi-electron system is conjugated with the second pi-electron system is to enable it to lower excitation energy of the third product.

With regard to such a reagent, it is preferred that the reagent have a third pi-electron system. An example of an advantage of using the reagent having the third pi-electron system is to enable it to ease the formation of the first product utilizing a simple reaction such as elimination reaction.

With regard to such a reagent, it is preferred that the third pi-electron system is not conjugated with the first pi-electron system. An example of an advantage of using the reagent in which the third pi-electron system is not conjugated with the first pi-electron system is to enable it to ease additionally the formation of the first product utilizing a simple reaction such as an elimination reaction.

With regard to such a reagent, it is preferred that the first pi-electron system is connected to the third pi-electron system through at least one carbon-carbon single bond or carbon atom in the reagent. An example of an advantage of using the reagent in which the third pi-electron system is connected to the first pi-electron system through at least one carbon atom is to enable it to ease additionally the formation of the first product utilizing a simple reaction such as elimination reaction.

A reagent relating to another aspect hereof is characterized by that: the reagent is capable of being a constituent of a composition; and the reagent is capable of generating a first chemical species through a process triggered by a feed of energy to at least one of the composition, a solution containing the composition and a film formed of the composition. An example of an advantage of using such a reagent is to enable it to utilize such a reagent as an initiator for a desired reaction process.

With regard to such a reagent, it is preferred that the reagent is capable of generating of the first chemical species by having a hydrogen atom of the reagent abstracted. An example of an advantage of using such a reagent is to enable it to ease additionally utilization of such a reagent as an initiator for a desired reaction process.

With regard to such a reagent, it is preferred that the feed of energy is carried out by a first exposure of the at least one of the composition, the solution and the film to at least one of a first electromagnetic ray of which wavelength is a first wavelength and a first particle ray. An example of an advantage of using such a reagent is to enable it to utilize easily such a reagent as an initiator for a desired reaction process.

With regard to such a reagent, it is preferred that the feed of energy is carried out by a first exposure of the at least one of the composition, the solution and the film to at least one of an extreme ultraviolet (EUV) light and an electron beam (EB). An example of an advantage of using such a reagent is to enable it to excite such a reagent at an exact position.

With regard to such a reagent, it is preferred that the first chemical species be capable of being excited by a second exposure of the at least one of the composition, the solution and the film by at least one of a second electromagnetic ray of which wavelength is a second wavelength and a second particle ray. An example of an advantage of using such a reagent is to enable it to induce reaction of the composition, the solution or the film even when the illuminance of the first electromagnetic ray or the first particle ray is not enough to excite the composition, the solution and the film containing the reagent.

With regard to such a reagent, it is preferred that the first chemical species be capable of being excited by a second exposure of the at least one of the composition, the solution and the film by at least one of a second electromagnetic ray of which wavelength is a second wavelength and a second particle ray; and the second wavelength is longer than the first wavelength. An example of an advantage of using such a reagent is to enable it to induce easily reaction of the composition, the solution or the film by exciting a product generated in the composition, the solution or the film by the first electromagnetic ray or the first particle ray even when the illuminance of the first electromagnetic ray or the first particle ray is not enough to excite the composition, the solution and the film.

With regard to such a reagent, it is preferred that the second wavelength is longer than 250 nm. An example of an advantage of using such a reagent is to enable it to excite the composition, the solution or the film by a light source commonly utilized such as mercury lamp and light-emitting diode.

With regard to such a reagent, it is preferred that the composition contains a precursor which is capable of generating a second chemical species. An example of an advantage of using such a reagent is to enable it to utilize such second chemical species as a trigger for a desired reaction.

With regard to such a reagent, it is preferred that the composition contains a precursor which is capable of generating a second chemical species by the second exposure. An example of an advantage of using such a reagent is to enable it to utilize easily such second chemical species as a trigger for a desired reaction.

A composition relating to an aspect hereof includes: a reagent which is capable of generating a first chemical species; and a precursor. It is preferred that: a first cutoff wavelength in a first absorption spectrum of the reagent is shorter than a second cutoff wavelength of a second absorption spectrum of the first chemical species; the precursor is capable of generating a second chemical species through an interaction between the precursor and the first chemical species. An example of an advantage of using such a composition is to enable it to: enhance electron-transfer or energy-transfer involved with the first chemical species to form the second chemical species because of higher level of the highest occupied molecular orbital (HOMO) or lower level of the lowest unoccupied molecular orbital; and utilize such second chemical species as a trigger for a desired reaction.

A composition relating to an aspect hereof includes any one of such a reagents mentioned above and any one of such precursors mentioned above.

A composition relating to an aspect hereof includes a reagent represented by formula (I); and a precursor.

(I)

In the formula (I), $R^1$ is a hydrogen atom; $R^2$ is a hydrogen atom, an alkyl group, an alkenyl group, an aryl group, an aralkyl group, an alkynyl group, an alkyl group containing a cyclic or polycyclic moiety, or a substituent containing at least one atom other than carbon atom and hydrogen atom; $R^3$ is a hydrogen atom, an alkyl group, an alkenyl group, an aryl group, an aralkyl group, an alkynyl group, an alkyl group containing a cyclic or polycyclic moiety, or a substituent containing at least one atom other than carbon atom and hydrogen atom; $R^4$ is a hydrogen atom, an alkyl group, an alkenyl group, an aryl group, an aralkyl group, an alkynyl group, an alkyl group containing a cyclic or polycyclic moiety, or a substituent containing at least one atom other than carbon atom and hydrogen atom; $R^5$ is a hydrogen atom, an alkyl group, an alkenyl group, an aryl group, an aralkyl group, an alkynyl group, an alkyl group containing a cyclic or polycyclic moiety, or a substituent containing at least one atom other than carbon atom and hydrogen atom; and $R^6$ is a hydrogen atom, an alkyl group, an alkenyl group, an aryl group, an aralkyl group, an alkynyl group, an alkyl group containing a cyclic or polycyclic moiety, or a substituent containing at least one atom other than carbon atom and hydrogen atom. An example of an advantage of using such a composition is to enable it to generate a reactive intermediate or chemical species from such a reagent because such a reagent has at least one hydrogen atom which can be abstracted.

With regard to such a composition, it is preferred that each of $R^2$ and $R^3$ is an aromatic group. An example of an advantage of such a composition is to enable it to enhance elimination of $R^1$ to form a chemical species. $R^2$ may be bonded to $R^3$ directly or indirectly through at least one atom such as carbon atom, oxygen atom, nitrogen atom and sulfur atom. This may contribute stabilization of such chemical species.

With regard to such a composition, it is preferred that each of $R^2$ and $R^4$ is an aromatic group. An example of an advantage of such a composition is to enable it to enhance elimination of $R^1$ to form a chemical species.

It is preferred that such a reagent has electron-donating group on such aromatic ring. Typical examples of electron-donating group are alkoxy group, hydroxy group, aryloxy group, alkylthio group, arylthio group, amino group having at least one of hydrogen atom, alkyl group and aryl group on the nitrogen atom.

With regard to such a composition, it is preferred that $R^6$ is capable of being eliminated after $R^1$ is eliminated. This may enable the composition to easily generate in situ a first product which is to be yielded from a first chemical species such as a reactive intermediate. An example of an advantage of using such a composition is to enable it to generate easily a first chemical species from such a reagent because such a reagent has at least one hydrogen atom of which abstraction reaction followed by the elimination of $R^6$ can occur.

With regard to such a composition, it is preferred that $R^1$ is capable of being abstracted by a reactive intermediate generated in at least one of the composition, a solution containing the composition and a film formed of the composition. An example of an advantage of using such a composition is to enable it to generate easily a chemical species from such a reagent because such a reagent has at least one hydrogen atom which can be abstracted by such reactive intermediate.

With regard to such a composition, it is preferred that $R^1$ is capable of being abstracted by a reactive intermediate generated in at least one of the composition, a solution containing the composition and a film formed of the composition by a first exposure of the at least one of the composition, the solution and the film to at least one of a first electromagnetic ray of which wavelength is a first wavelength and a first particle ray. An example of an advantage of using such a composition is to enable it to generate easily a chemical species from such a reagent by utilizing an abstraction reaction of $R^1$ by a reactive intermediate generated by the first exposure.

With regard to such a composition, it is preferred that the reagent is capable of a first chemical species by having $R^1$ is abstracted by the reactive intermediate; and the precursor is capable of a second chemical species by an interaction between the first chemical species and the precursor under a second exposure of the at least one of the composition, the solution and the film to at least one of a second electromagnetic ray of which wavelength is a second wavelength and a second particle ray. An example of an advantage of using such a composition is to enable it to generate easily the second chemical species by utilizing such interaction between the first chemical species and the precursor enhanced by the second exposure.

A composition relating to an aspect hereof includes: a reagent; and a precursor. It is preferred that the reagent includes a first group including an aryl group and a second group including a hydrogen and a carbon atom bonded to the first group; and the hydrogen atom is bonded to the carbon atom. An example of an advantage of using such a composition is to enable it to form a chemical species or product having a larger pi-electron system through an elimination of such hydrogen atom. Such chemical species or product can enhance formation of a chemical species from the precursor.

With regard to such a composition, it is preferred that the precursor is a photoacid generator (PAG). An example of an advantage of using such a composition is to enable it to generate easily acid.

With regard to such a composition, it is preferred that the precursor is an organic salt containing an iodonium ion or a sulfonium ion. An example of an advantage of using such a composition is to enable it to form strong acid such as triflate, nonaflate and hexafluorophosphate.

With regard to such a composition, it is preferred that a difference between at least one of a first oxidation potential of a ground state and a second oxidation potential of an excited state of the first chemical species and at least one of a first reduction potential of a ground state and a second reduction potential of an excited state of the precursor is equal to or greater than 0.10 eV. An example of an advantage of using such a composition is to enable it to generate a chemical species from the precursor through an electron-transfer between the first chemical species and the precursor.

With regard to such a composition, it is preferred that a first reduction potential of a ground state of the precursor is smaller than at least one of a first oxidation potential of a ground state of the first chemical species and a second oxidation potential of an excited state of the first chemical species. An example of an advantage of using such a composition is to enable it to generate a chemical species from the precursor through an electron-transfer from the first chemical species to the precursor.

With regard to such a composition, it is preferred that the first chemical species has a reducing character. An example of an advantage of using such a composition is to enable it to generate a chemical species from the precursor through an electron-transfer from the first chemical species to the precursor.

With regard to such a composition, it is preferred that the first chemical species discharges at least one of a hydrogen atom and a hydrogen ion that has a reducing character. An example of an advantage of using such a composition is to enable it to generate a chemical species from the precursor by the reduction of the precursor by such reducing chemical species.

In certain embodiments relating to an aspect hereof, a composition includes: a reagent represented by formula (II); and a precursor that can function as a generation source of acid.

(II)

In the formula (I), it is preferred that: $R^7$ is a hydrogen atom; $R^8$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom; $R^9$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom; and $R^{10}$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom.

With regard to the reagent represented by formula (II), it is preferred that at least one of $R^8$ and $R^9$ is an aromatic group. An example of an advantage of such a reagent is to enable it to induce easily elimination of $R^7$ to form a desired chemical species or reactive intermediate. $R^8$ may be bonded to $R^9$ directly or indirectly through at least one atom such as carbon atom, oxygen atom, nitrogen atom and sulfur atom. This may contribute stabilization of such chemical species.

The reagent represented by formula (II) can be added to such a composition as its derivative having a protecting group such as methoxy methyl group, benzyl group, trialkylsilyl group, acetyl group, benzoyl group and triphenyl methyl group in order to improve preservation stability. The reagent can be generated in situ.

Typical examples of such a reagent are the following compounds which have electron-donating group on the aromatic groups.

Other typical examples of electron-donating group are alkoxy group, hydroxy group, aryloxy group, alkylthio group, arylthio group, amino group having at least one of hydrogen atom, alkyl group and aryl group on the nitrogen atom.

A method for manufacturing a device relating to an aspect hereof includes: applying a solution of any one of such a compositions mentioned above to a member such that a film including the composition is formed on the member; and first exposing the film to at least one of the first electromagnetic ray and the first particle ray such that a first portion of the film is exposed to the at least one of the first electromagnetic ray and the first particle ray while a second portion of the film is not exposed to the at least one of the first electromagnetic ray and the first particle ray; and second exposing the film to at least one of a second electromagnetic ray and a second particle ray such that the first portion of the film is exposed to the at least one of the second electromagnetic ray and the second particle ray. An example of an advantage of using such method is to enable it to induce reaction of the film even when the illuminance of the first electromagnetic ray or the first particle ray is not enough to excite the composition, the solution and the film containing the reagent.

With regard to such method it is preferred that the second exposing is carried out such that at least a part of the second portion is exposed to the at least one of the second electromagnetic ray and the second particle ray. An example of an advantage of using such method is to enable it to perform the second exposing without any mask.

With regard to such method, it is preferred that the second exposing is carried out such that a first area including the first portion of the film exposed to the at least one of the first electromagnetic ray and the first particle ray is smaller than a second area including the first portion of the film exposed to the at least one of the second electromagnetic ray and the second particle ray. An example of an advantage of using such method is to enable it to perform the second exposing with lower resolution compared to the first exposing.

With regard to such method, it is preferred that such method, further includes removing the first portion or the second portion. An example of an advantage of using such method is to enable it to perform a patterning process with negative or positive resist.

With regard to such method, it is preferred that further includes: etching the member such that a third portion of the member on which the first portion or second portion have been present is etched.

With regard to such method, it is preferred that the first electromagnetic ray and the first particle ray are an extreme ultraviolet (EUV) light and an electron beam (EB), respectively. An example of an advantage of using such method is to enable it to perform a patterning process with high resolution.

A reagent relating to an aspect hereof is able to produce a reactive intermediate enhancing generation of a chemical species such as acid and base. Typical examples of acid are triflate, nonaflate, hexafluorophosphate and hexafluoroantimonate. Typical examples of base are hydroxide ion and amines. Several photobase generators can be used as precursors of base. Among them, the following compounds having higher electro-accepting nature or an electron-accepting substituent are often preferred as precursors of base for compatibility with such a reagent.

Typically, the first chemical species generated from any one of reagents mentioned above can assist the generation of Brönsted acid or base from a precursor. Furthermore, such a reagent can apply to the generation of Lewis acid and base. Typically, the first chemical species is formed directly or indirectly by an exposure of the reagent to an electromagnetic ray or a particle ray. More typically, an extreme ultraviolet (EUV) light and electron beam (EB) are used for such electromagnetic ray and particle ray, respectively. The precursor generates such chemical species through the electron transfer involved with the first chemical species. Such a reagent may have a hydrogen atom easily abstracted character by unstable radical species and the first chemical species generated from reagent may have reducing character.

Typically, such a reagent is capable of generating a carbon radical stabilized by α-aryl functional groups. Examples for such a reagents are benzyl derivatives, α-aryl-α-alkyl derivatives, α-diaryl-alkyl derivatives, α-diaryl-β-aryl alkyl derivatives, α-diaryl-β-diaryl alkyl derivatives. Such stabilized carbon radical transfers its electron to PAG due to the reducing character. It is preferred that such a reagent has at least one electron-donating group. It is more preferable that such a reagent has at least one aromatic group and at least one electron-donating group on the at least one aromatic group. This can improve the electron-donating ability of such radicals or chemical species generated from such a reagent.

Typical examples of electron-donating group are alkoxy group, hydroxy group, aryloxy group, alkylthio group, arylthio group, amino group having at least one of hydrogen atom, alkyl group and aryl group on the nitrogen atom.

A composition containing such a reagent which is to form a first chemical species, a precursor which is to form a second chemical species, and a compound that is to react with the second chemical species can be applied as a photoresist such as chemically-amplified resist (CAR) to manufacturing of electronic devices such as semiconductor device and electro-optical device.

BRIEF DESCRIPTION OF THE DRAWINGS

In the drawings, which illustrate what is currently considered to be the best mode for carrying out the invention.

DETAILED DESCRIPTION

The invention is further explained with the aid of the following illustrative examples.

Experimental Procedures

Synthesis of 2-isopropenyl-1,3,5-trimethoxy-benzene 2.00 g of 2,4,6-trimethoxyacetophenone and 3.74 g of methyltriphenyphosphonium bromide are added to 20 g of tetrahydrofuran. 2.13 g of potassium tert-butoxide is added to the tetrahydrofuran mixture containing 2,4,6-trimethoxyacetophenone and methyltriphenyphosphonium bromide. The mixture is stirred at 60 degrees Celsius for 2 hours and the mixture is filtrated. Afterwards, the tetrahydrofuran is distilled away and 20 g of cyclohexane is added to the residue. The cyclohexane mixture is stirred for 10 minutes and a deposit is filtrated and the filtrate is collected. Thereafter, cyclohexane is distilled away, and the resultant is purified by silica gel column chromatography (ethyl acetate:hexane=10:90). Thereby 1.62 g of 2-isopropenyl-1,3,5-trimethoxy-benzene is obtained.

Synthesis of 2-isopropyl-1,3,5-trimethoxy-benzene (Reagent 1)

1.50 g of 2-isopropenyl-1,3,5-trimethoxy-benzene and 0.08 g of 5% palladium carbon are added to 15.0 g of ethyl acetate. The mixture is stirred at 25 Celsius degrees for 3 hours in 1 atm hydrogen atmosphere. Afterwards, the mixture is filtrated and the filtrate is collected. Thereafter, ethyl acetate is distilled away, and the resultant is purified by silica gel column chromatography (ethyl acetate:hexane=5:95). Thereby 2.20 g of 2-isopropyl-1,3,5-trimethoxy-benzene is obtained.

Reagent 1

Synthesis of 9-benzylidene-9H-thioxanthene 4.00 g of thioxanthone and 8.06 g of benzyltriphenyphosphonium chloride are added to 40.0 g of tetrahydrofuran. 3.17 g of potassium tert-butoxide is added to the tetrahydrofuran mixture containing thioxanthone and benzyltriphenyphosphonium chloride. The mixture is stirred at 25 degrees Celsius for 140 hours and the mixture is filtrated. Afterwards, the tetrahydrofuran is distilled away and 40 g of cyclohexane is added to the residue. The cyclohexane mixture is stirred for 10 minutes and a deposit is filtrated and the filtrate is collected. Thereafter, cyclohexane is distilled away, and the resultant is purified by silica gel column chromatography (ethyl acetate:hexane=1:99). Thereby 2.91 g of 9-benzylidene-9H-thioxanthene is obtained.

Synthesis of 9-benzyl-9H-thioxanthene (Reagent 2)

2.80 g of 9-benzylidene-9H-thioxanthene and 0.14 g of 5% palladium carbon are added to 28.0 g of ethyl acetate. The mixture is stirred at 40 Celsius degrees for 12 hours in 1 atm hydrogen atmosphere. Afterwards, the mixture is filtrated and the filtrate is collected. Thereafter, ethyl acetate is distilled away, and the resultant is purified by silica gel column chromatography (ethyl acetate:hexane=1:99). Thereby 2.62 g of 9-benzyl-9H-thioxanthene is obtained.

Reagent 2

Synthesis of 3-(2,4,6-trimethoxy-phenyl)-but-2-en-1-ol 4.00 g of 2,4,6-trimethoxyacetophenone and 8.10 g of (2-hydroxyethyl)triphenyphosphonium bromide are added to 40 g of tetrahydrofuran. 3.80 g of 40% aqueous sodium hydroxide is added to the tetrahydrofuran mixture containing 2,4,6-trimethoxyaetophenone and (2-hydroxyethyl)triphenyphosphonium bromide. The mixture is stirred at 60 degrees Celsius for 4 hours and the mixture is filtrated. Afterwards, the tetrahydrofuran is distilled away and 40 g of cyclohexane is added to the residue. The cyclohexane mixture is stirred for 10 minutes and a deposit is filtrated and the filtrate is collected. Thereafter, cyclohexane is distilled away, and the resultant is purified by silica gel column chromatography (ethyl acetate:hexane=10:90). Thereby 3.49 g of 3-(2,4,6-trimethoxy-phenyl)-but-2-en-1-ol is obtained.

Synthesis of 3-(2,4,6-trimethoxy-phenyl)-butan-1-ol 3.30 g of 3-(2,4,6-trimethoxy-phenyl)-but-2-en-1-ol and 0.17 g of 5% palladium carbon are added to 33.0 g of ethyl acetate. The mixture is stirred at 25 Celsius degrees for 4 hours in 1 atm hydrogen atmosphere. Afterwards, the mixture is filtrated and the filtrate is collected. Thereafter, ethyl acetate is distilled away, and the resultant is purified by silica gel column chromatography (ethyl acetate:hexane=10:90). Thereby 3.10 g of 3-(2,4,6-trimethoxy-phenyl)-butan-1-ol is obtained.

Synthesis of 2-methyl-acrylic acid 3-(2,4,6-trimethoxy-phenyl)-butyl ester (Reagent 3)

3.00 g of 3-(2,4,6-trimethoxy-phenyl)-butan-1-ol and 2.12 g of methacrylic anhydride are dissolved in 21 g of tetrahydrofuran. 1.52 g of triethylamine dissolved in 4.55 g of tetrahydrofuran is added dropwise to the tetrahydrofuran solution containing 3-(2,4,6-Trimethoxy-phenyl)-butan-1-ol over 10 minutes. After that the mixture is stirred at 25 degrees Celsius for 3 hours. Since then, the mixture is further stirred after addition of water. Then extracted with 60 g ethyl acetate and the organic phase is washed with water. Thereafter, ethyl acetate is distilled away, and the residue is purified by silica gel column chromatography (ethyl acetate:hexane=1:9). Thereby 3.12 g of 2-methyl-acrylic acid 3-(2,4,6-trimethoxy-phenyl)-butyl ester is obtained.

Reagent 3

A solution containing 5.0 g of α-methacryloyloxy-γ-butylolactone, 6.03 g of 2-methyladamantane-2-methacrylate, and 4.34 g of 3-hydroxyadamantane-1-methacrylate, 0.51 g of dimethyl-2,2'-azobis(2-methylpropionate), and 26.1 g of tetrahydrofuran is prepared. The prepared solution is added dropwise over 4 hours to 20.0 g of tetrahydrofuran placed in flask with stirring and boiling. After the addition of the prepared solution, the mixture is heated to reflux for 2 hours and cooled to room temperature. Addition of the mixture by drops to a mixed liquid containing 160 g of hexane and 18 g of tetrahydrofuran with vigorously stirring precipitates the copolymer. The copolymer is isolated by filtration. Purification of the copolymer is carried out by vacuum drying following twice washings by 70 g of hexane, and thereby 8.5 g of white powder of the copolymer (Resin A) is obtained.

Resin A

A solution containing 1.20 g of 2-methyl-acrylic acid 3-(2,4,6-trimethoxy-phenyl)-butyl ester, 9.27 g of α-methacryloyloxy-γ-butylolactone, 9.12 g of 2-methyladamantane-2-methacrylate, 7.67 g of 3-hydroxyadamantane-1-methacrylate, 0.30 g of butyl mercaptane, 1.49 g of dimethyl-2,2'-azobis(2-methylpropionate) and 22.8 g of tetrahydrofuran is prepared. The prepared solution is added dropwise over 4 hours to 8.0 g of tetrahydrofuran placed in flask with stirring and boiling. After the addition of the prepared solution, the mixture is heated to reflux for 2 hours and cooled to room temperature. Addition of the mixture by drops to a mixed liquid containing 287 g of hexane and 32 g of tetrahydrofuran with vigorously stirring precipitates the copolymer. The copolymer is isolated by filtration. Purification of the copolymer is carried out by vacuum drying following twice washings by 100 g of hexane, and thereby 19.9 g of white powder of the copolymer (Resin B) is obtained.

Resin B

B-1

B-2

Preparation of Samples for Evaluation (the "Evaluation Samples")

Each of Evaluation Samples 1-8 contains 15.0 mg of coumarin 6 as an indicator for acid generation and 2000 mg of cyclohexanone. Each of Evaluation Samples 1-3 and 7 contains 0.043 mmol of diphenyliodonium nonafluorobutanesulfonate (DPI-PFBS) as a photoacid generator (PAG) while each of Evaluation Samples 4-6 and 8 contains 5-phenyl-dibenzothiophenium nonafluorobutanesulfonate (PBpS-PFBS) as a PAG. Each of Evaluation Samples 1-6 contains 300 mg of Resins A while Evaluation Samples 7 and 8 contain 300 mg of Resin B. Evaluation Samples 2 and 5 contain 0.087 mmol of Reagent 1 while Evaluation Samples 3 and 6 contain 0.087 mmol of Reagent 2, Table 1 shows the summary of constituents of Evaluation Samples 1-8.

TABLE 1

Samples for evaluation for efficiencies of patterning

| | Resin | PAG | Additive | Solvent |
|---|---|---|---|---|
| Evaluation Sample 1 | Resin A | DPI-PFBS | — | Cyclohexanone |
| Evaluation Sample 2 | | | Reagent 1 | |
| Evaluation Sample 3 | | | Reagent 2 | |
| Evaluation Sample 4 | | PBpS-PFBS | | |
| Evaluation Sample 5 | | | Reagent 1 | |
| Evaluation Sample 6 | | | Reagent 2 | |
| Evaluation Sample 7 | Resin B | DPI-PFBS | — | |
| Evaluation Sample 8 | | PBpS-PFBS | — | |

Evaluation of Efficiency of Acid Generation

Films are formed on 4-inch quartz wafers by spin-coating of Evaluation Samples. Two runs are carried out for each of Evaluation Samples 1-8. For one run of the two runs, an exposure of a film to a series of electron beams of which volumes are 0, 10, 20, 30, and 40 $\mu C/cm^2$ output from an electron beam (EB) lithography apparatus is carried out. For the other run of the two runs, such EB exposure and an exposure to a UV light (3ω of Nd: YAG laser) with a delay of a predetermined amount of time (5 μs) from the EB exposure are carried out.

Subsequent to the EB exposure (if any, the UV exposure), the efficiency of acid generation for the film is obtained by plotting absorbances at 534 nm which are indicators of quantities of protonated coumarin 6 generated by the EB exposures (if any, the UV exposure) with the respective volumes.

Table 2 shows the relative acid-generation efficiencies for Evaluation Samples 1-8. For the runs 2, 4, 6, 8, 10, 12, 14, 16 and 18, in addition to an EB exposure, an UV exposure (1000 $mJ/cm^2$) is carried out with a delay of 5 μs from the EB exposure. In Table 2, the acid-generation efficiency for Run 1 is used as a benchmark.

As the runs 3-6 and 9-16 indicates, additions of Reagent 1, Reagent 2 and Resin B containing B-1 moiety improves the acid generation efficiencies. This indicates that Reagent 1, Reagent 2 and B-1 moiety of Resin B act as acid generation enhancers (AGEs).

The PAGs are considered to be reduced by radicals each of which has unpaired electron present in a carbon atom bonded to an aryl group generated from Reagent 1, Reagent 2 and B-1 moiety of Resin B by the EB exposures.

From comparisons of runs 3, 4, 5, 6, 13 and 14 with runs 9, 10, 11, 12, 15 and 16, respectively, acid generation efficiencies for DPI-PFBS is found to be greater than those for PBpS-PFBS. This is thought to be due to the higher electron-accepting ability of DPI-PFBS compared to PBpS-PFBS.

For runs 4, 6, 10, 12, 14 and 16 higher acid generation efficiencies are observed compared runs 3, 5, 9, 11, 13 and 15, respectively. This indicates that excitation of such radicals improve additionally acid generation efficiencies.

Reagent 1 is considered to have a level of a highest occupied molecular orbital (HOMO) similar to that of B-1 moiety of Resin B. However, acid generation efficiencies of Evaluation Samples 7 and 8 containing Resin B are higher than those of Evaluation Samples containing Reagent 1.

This implies that the homogeneous dispersion of AGE (such as B-1) moieties into the polymer matrix improves acid generation efficiency.

TABLE 2

The relative acid-generation efficiencies for the Evaluation Samples 1-8

| Run | Evaluation Sample | Relative Efficiency |
|---|---|---|
| 1 | 1 | 1.00 |
| 2 | | 1.00 |
| 3 | 2 | 1.20 |
| 4 | | 1.30 |
| 5 | 3 | 1.10 |
| 6 | | 1.30 |
| 7 | 4 | 0.90 |
| 8 | | 0.90 |
| 9 | 5 | 0.98 |
| 10 | | 1.10 |
| 11 | 6 | 0.95 |
| 12 | | 1.10 |
| 13 | 7 | 1.26 |
| 14 | | 1.38 |
| 15 | 8 | 1.00 |
| 16 | | 1.14 |

Figure 1:
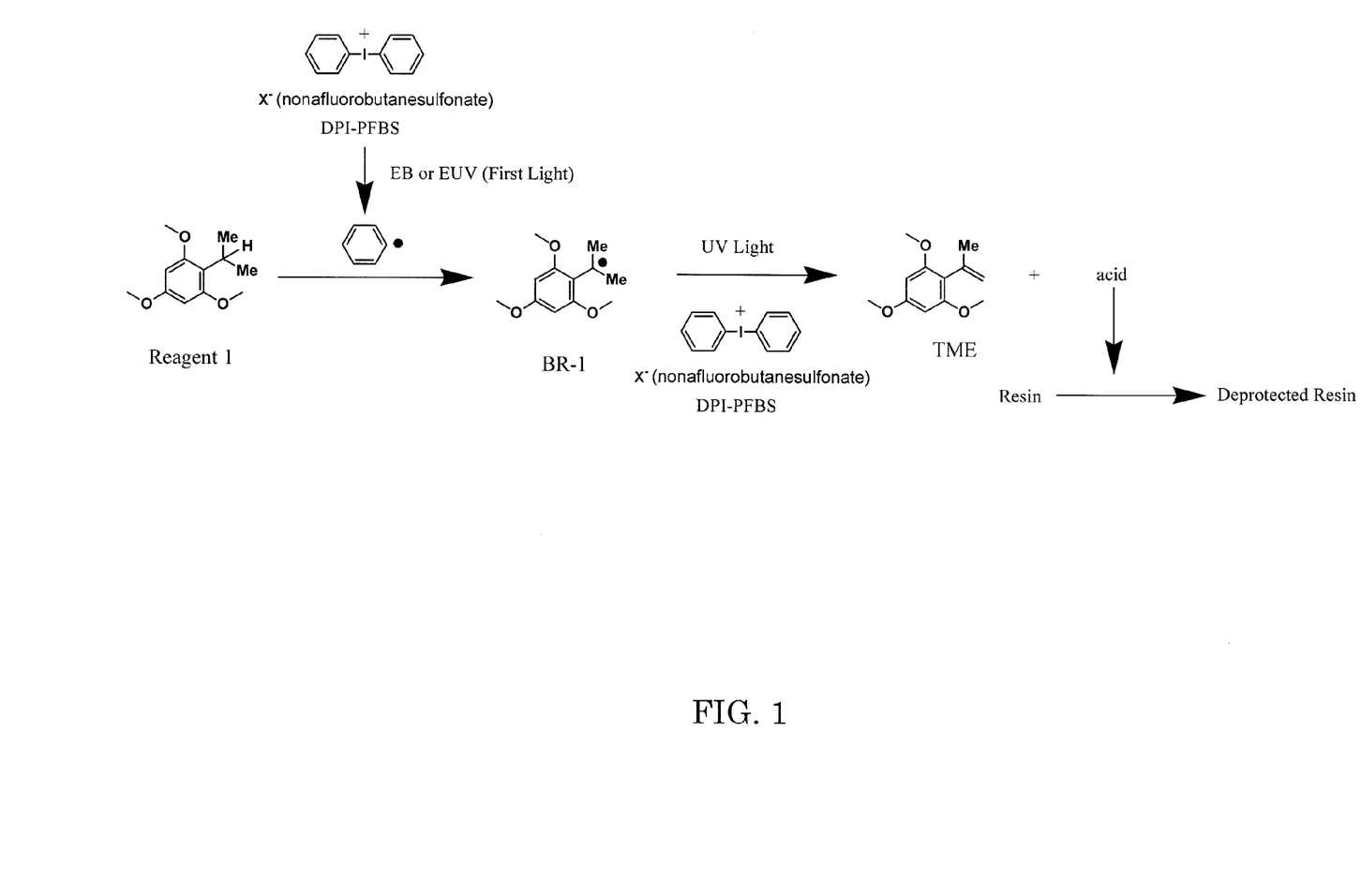
FIG. 1 shows a typical reaction scheme of a composition containing a reagent relating to an aspect hereof.

FIG. 1 shows a typical reaction scheme of a composition containing a Reagent 1 and DPI-PFBS as a PAG. An exposure of the composition to an EUV or EB yields a radical such as phenyl radical generated by decomposition of the PAG. A hydrogen atom bonded to a carbon atom bonded to an aromatic group of Reagent 1 is abstracted by phenyl radical to form a radical BR-1 of which unpaired electron is present in the carbon bonded to the aromatic group. In other words, a benzyl-type radical is generated.

The radical BR-1 donates an electron the PAG. Such electron-donation to the PAG, which yields acid, is additionally enhanced by an excitation of the radical BR-1. Through such electron-donation to the PAG, the radical BR-1 is converted into TME which has one carbon-carbon multiple bond bonded to the aromatic group. The conversion to TME from BR-1 is accompanied with an elimination of a group such as hydrogen atom. Acid generated from the PAG deprotects resin contained in the composition.

Figure 2:
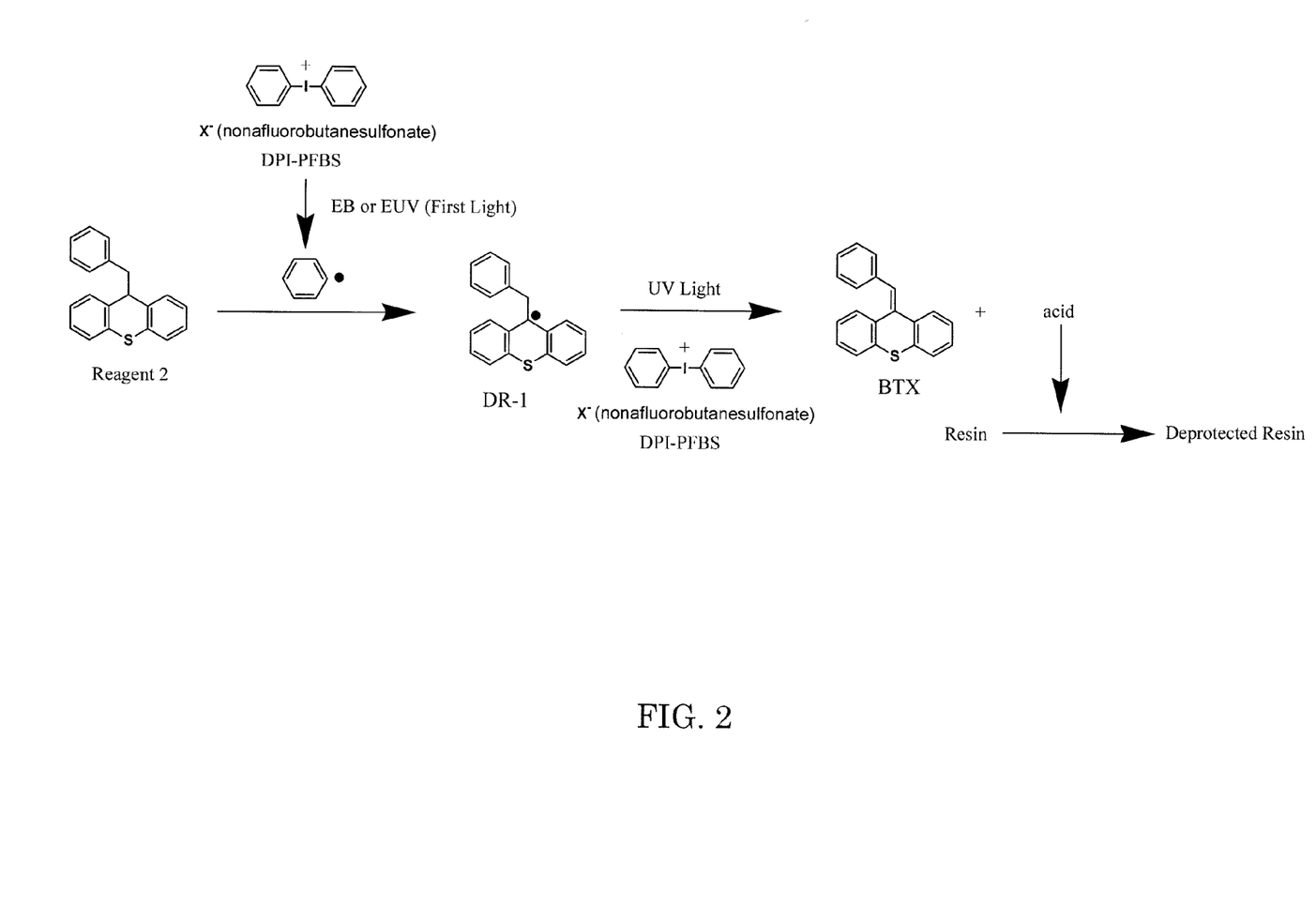
FIG. 2 shows a typical reaction scheme of a composition a reagent relating to another aspect hereof.

FIG. 2 shows a typical reaction scheme of a composition containing a Reagent 2 and DPI-PFBS as a PAG. An exposure of the composition to an EUV or EB yields a radical such as phenyl radical generated by decomposition of the PAG. A hydrogen atom bonded to a carbon atom bonded to two aromatic groups of Reagent 2 is abstracted by phenyl radical to form a radical DR-1 of which unpaired electron is present in the carbon bonded to the two aromatic groups. In other words, a benzyl-type radical is generated.

The radical DR-1 donates an electron the PAG. Such electron-donation to the PAG, which yields acid, is additionally enhanced by an excitation of the radical DR-1. Through such electron-donation to the PAG, the radical DR-1 is converted into BTX which has one carbon-carbon multiple bond bonded to the two aromatic groups. The conversion to BTX from Dr-1 is accompanied with an elimination of a group such as hydrogen atom. Acid generated from the PAG deprotects resin contained in the composition.

Figure 3:
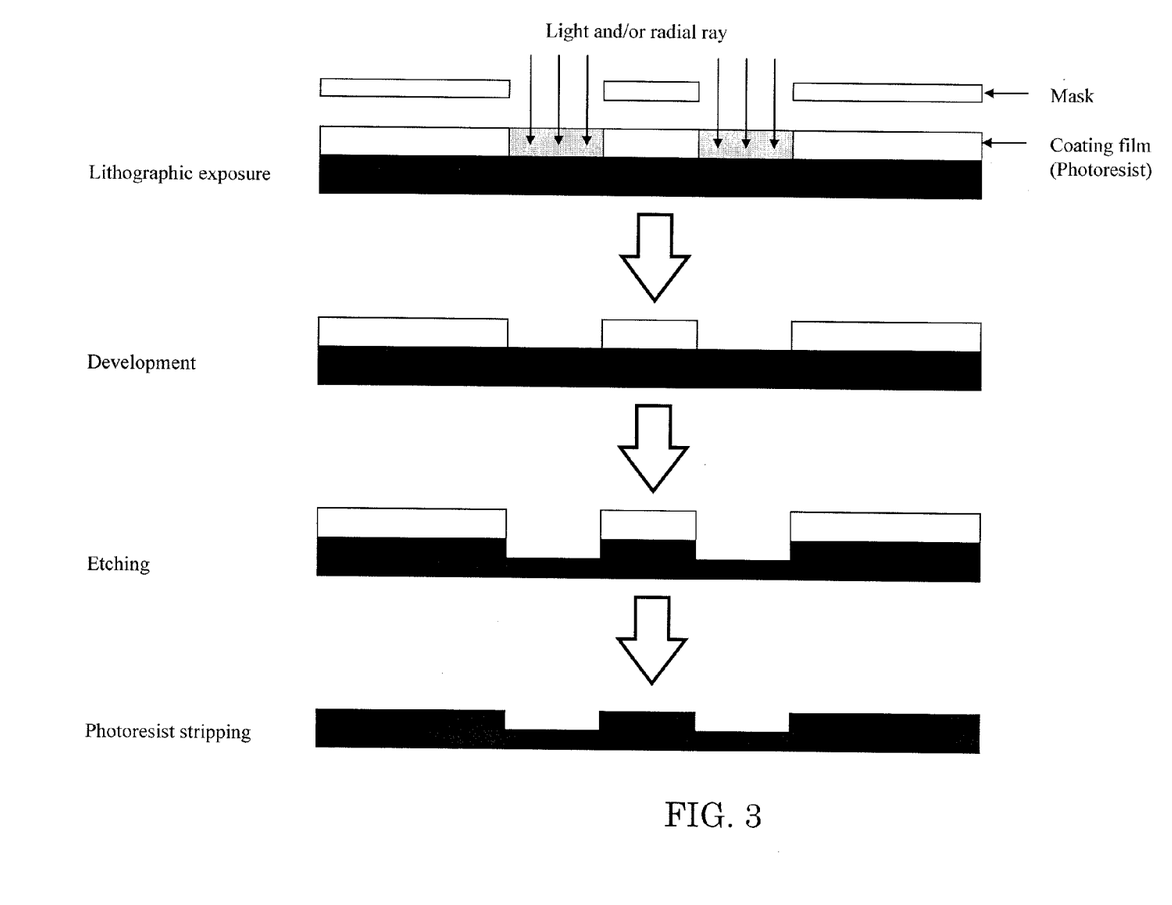
FIG. 3 shows fabrication processes of a device such as integrated circuit (IC) using a CAR containing a reagent relating to an aspect hereof.

FIG. 3 shows fabrication processes of a device such as integrated circuit (IC) by using a chemically-amplified resist (CAR) containing Reagent 1.

A silicon wafer is provided. The surface of silicon wafer is oxidized by heating the silicon wafer in the presence of oxygen gas.

A solution of the CAR containing Reagent 2 is applied to the surface of an Si wafer by spin coating to form a coating film. The coating film is prebaked.

Then, an irradiation of the coating film with a EUV light through a mask and an irradiation of a part including an irradiated portion with the EUV light of the coating film with a 3ω of Nd: YAG Laser is carried out with 5-10 μs of a delay from the EUV irradiation. In other words, a transient excitation of the coating film is carried out by using the 3ω of Nd: YAG Laser.

After the irradiation of the coating film with the EUV light and the transient excitation are carried out, development of the coating film which has been irradiated with the EUV light and the 3ω of Nd: YAG Laser is performed.

The coating film and the silicon wafer are exposed to plasma. After that, the remaining film is removed.

An electronic device such as integrated circuit is fabricated utilizing the processes shown in FIG. 3. The deterioration of the device due to the irradiation with a light is suppressed compared to existing photoresists since times for the irradiation of the coating film is shortened by using the transient excitation.

What is claimed is:

1. A composition comprising:
a photoacid generator having iodonium salt or sulfonium salt;
a compound having a protecting group capable of being deprotected by the acid; and
a reagent with a first structure forming a carbon radical, wherein a first cutoff wavelength in a first absorption spectrum of the reagent is shorter than a second cutoff wavelength of a second absorption spectrum of the carbon radical, and wherein the reagent is represented by Formula (I) or Formula (II):

Formula (I)

wherein:
$R^2$ is a phenyl group;
$R^3$ is an alkyl group or a phenyl group;
at least one phenyl group of $R^2$ and $R^3$ has at least one electron-donating group selected from the group consisting of an alkoxy group, a hydroxy group, an aryloxy group, an alkylthio group, an arylthio group, and an amino group having at least one of a hydrogen atom, an alkyl group, and an aryl group on a nitrogen atom of the amino group;
each of $R^4$ and $R^5$ is independently selected from the group consisting of a hydrogen atom, an alkyl group, and a phenyl group; and
$R^2$ may be bonded to $R^3$ directly or indirectly through at least one atom selected from the group consisting of a carbon atom, an oxygen atom, a nitrogen atom, and a sulfur atom;

Formula (II)

wherein:
$R^8$ is a phenyl group;
$R^9$ is an alkyl group or a phenyl group;
at least one of the phenyl groups of $R^8$ and $R^9$ has at least one electron-donating group selected from the group consisting of an alkoxy group, a hydroxy group, an aryloxy group, an alkylthio group, an arylthio group, and an amino group having at least one of a hydrogen atom, an alkyl group, and an aryl group on a nitrogen atom of the amino group;
wherein:
one of $R^9$ and the electron-donating group may be bonded with a (meth)acryloyloxy alkyl group; and
$R^8$ may be bonded to $R^9$ directly or indirectly through at least one atom selected from the group consisting of a carbon atom, an oxygen atom, a nitrogen atom and a sulfur atom,
wherein the reagent includes at least one selected from the group consisting of -continued , and 2. The composition of claim 1, wherein the compound is a copolymer with the first structure as a unit.

3. A method of manufacturing a device, comprising:
preparing the composition of claim 1;
forming a film by coating the composition on a wafer;
exposing a first portion of the film to at least one of a first electromagnetic ray and a first particle ray, while a second portion of the film is not exposed to the at least one of the first electromagnetic ray and the first particle ray; and
exposing at least a portion of the first portion of the film to at least one of a second electromagnetic ray and a second particle ray.

4. The method of claim 3, further comprising:
developing the film to remove the first portion of the film and expose at least a portion of the wafer.

5. The method of claim 4, further comprising:
etching the exposed portions of the wafer.

6. The method of claim 3, wherein the first electromagnetic ray and the first particle ray are an extreme ultraviolet (EUV) light and an electron beam (EB), respectively.

7. A composition comprising:
a reagent represented by Formula (I) or Formula (II):

Formula (I)

wherein:
$R^2$ is a phenyl group;
$R^3$ is an alkyl group or a phenyl group;
each of $R^4$ and $R^5$ is independently selected from the group consisting of a hydrogen atom, an alkyl group, and a phenyl group;
at least one phenyl group of $R^2$ and $R^3$ has at least one electron-donating group selected from the group consisting of an alkoxy group, a hydroxy group, an aryloxy group, an alkylthio group, an arylthio group, and an amino group having at least one of a hydrogen atom, an alkyl group, and an aryl group on a nitrogen atom of the amino group; and one of $R^3$-$R^5$ and the electron-donating group may be bonded with a (meth)acryloyloxy alkyl group;

Formula (II)

wherein:
$R^8$ is a phenyl group;
$R^9$ is an alkyl group or a phenyl group;
at least one phenyl group of $R^8$ and $R^9$ has at least one electron-donating group selected from the group consisting of an alkoxy group, a hydroxy group, an aryloxy group, an alkylthio group, an arylthio group, and an amino group having at least one of a hydrogen atom, an alkyl group, and an aryl group on a nitrogen atom of the amino group;
one of $R^9$ and the electron-donating group may be bonded with a (meth)acryloyloxy alkyl group; and
a resin,
wherein the reagent includes at least one selected from the group consisting of , and

.

8. A reagent represented by Formula (I) or Formula (II):

Formula (I)

wherein:

R² is a phenyl group;

R³ is an alkyl group or a phenyl group;

each of R⁴ and R⁵ is independently selected from the group consisting of a hydrogen atom, an alkyl group, and a phenyl group;

at least one phenyl group of R² and R³ is an aryl group having at least one electron-donating group selected from the group consisting of an alkoxy group, a hydroxy group, an aryloxy group, an alkylthio group, an arylthio group, and an amino group having at least one of a hydrogen atom, an alkyl group, and an aryl group on a nitrogen atom of the amino group;

one of R³-R⁵ and the electron-donating group may be bonded with a (meth)acryloyloxy alkyl group; and R² may be bonded to R³ directly or indirectly through at least one atom selected from the group consisting of a carbon atom, an oxygen atom, a nitrogen atom and a sulfur atom;

Formula (II)

wherein:

R⁸ is a phenyl group;

R⁹ is an alkyl group or a phenyl group;

at least one phenyl group of R⁸ and R⁹ has at least one electron-donating group selected from the group consisting of an alkoxy group, a hydroxy group, an aryloxy group, an alkylthio group, an arylthio group, and an amino group having at least one of a hydrogen atom, an alkyl group, and an aryl group on a nitrogen atom of the amino group;

one of R⁹ and the electron-donating group may be bonded with a (meth)acryloyloxy alkyl group; and R⁸ may be bonded to R⁹ directly or indirectly through at least one atom selected from the group consisting of a carbon atom, an oxygen atom, a nitrogen atom and a sulfur atom, wherein the reagent includes at least one selected from the group consisting of 9. A method of manufacturing a device, the method comprising:
   preparing the composition of claim 7;
   forming a film by coating the composition onto a wafer;
   exposing a first portion of the film to at least one of a first electromagnetic ray and a first particle ray, while a second portion of the film is not exposed to the at least one of the first electromagnetic ray and the first particle ray; and
   exposing at least a part of the second portion to at least one of a second electromagnetic ray and a second particle ray.

10. A composition comprising:
    a photoacid generator; and
    a compound including a resin having a structure wherein at least one reagent of claim 8 is bonded to a polymer chain of the resin via a linking group.

* * * * *